(12) United States Patent
Demuth et al.

(10) Patent No.: US 7,060,719 B2
(45) Date of Patent: Jun. 13, 2006

(54) GLUTAMINYL BASED DPIV INHIBITORS

(75) Inventors: Hans-Ulrich Demuth, Halle/Saale (DE); Torsten Hoffmann, Halle/Saale (DE); Ulrich Heiser, Halle/Saale (DE)

(73) Assignee: Prosidion Limited, Oxford (GB)

( * ) Notice: Subject to any disclaimer, the term of this patent is extended or adjusted under 35 U.S.C. 154(b) by 0 days.

(21) Appl. No.: 10/779,158

(22) Filed: Feb. 13, 2004

(65) Prior Publication Data

US 2004/0167191 A1    Aug. 26, 2004

Related U.S. Application Data

(63) Continuation of application No. 10/244,347, filed on Sep. 16, 2002.

(60) Provisional application No. 60/360,909, filed on Feb. 28, 2002.

(30) Foreign Application Priority Data

Jun. 27, 2002    (EP) .................... PCT/EP02/07124

(51) Int. Cl.
*A61K 31/425* (2006.01)
*A61K 31/40* (2006.01)
*C07D 277/04* (2006.01)
*C07D 207/00* (2006.01)

(52) U.S. Cl. .................. 514/365; 514/423; 548/200; 548/531

(58) Field of Classification Search ............... 548/200, 548/531; 514/365, 423
See application file for complete search history.

(56) References Cited

U.S. PATENT DOCUMENTS 6,548,481 B1 * 4/2003 Demuth et al. ............... 514/19
6,849,622 B1 * 2/2005 Yasuda et al. ......... 514/217.08

* cited by examiner

*Primary Examiner*—Deborah C. Lambkin
(74) *Attorney, Agent, or Firm*—Shu M. Lee

(57) ABSTRACT

The present invention provides compounds of the formula:

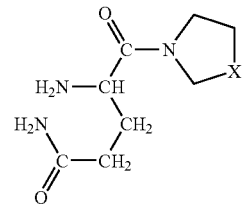

wherein $X=CH_2$ or S or pharmaceutical acceptable salts thereof useful for treating conditions mediated by DPIV or DPIV-like enzymes, such as arthritis, obesity, immune and autoimmune disorders, allograft transplantation, cancer, neuronal disorders and dermal diseases.

18 Claims, 6 Drawing Sheets

GLUTAMINYL BASED DPIV INHIBITORS

This application is a continuation of U.S. application Ser. No. 10/244,347 filed on Sep. 16, 2002, which is incorporated herein by reference in its entirety which claims the benefit of provisional application Ser. No. 60/360,909 filed Feb. 28, 2002.

FIELD OF THE INVENTION

The present invention relates to the area of dipeptidyl peptidase IV inhibition and, more particularly, relates to glutaminyl pyrrolidine and glutaminyl thiazolidine, pharmaceutical compositions containing said compounds, and the use of said compounds in inhibiting dipeptidyl peptidase IV and dipeptidyl peptidase IV-like enzyme activity.

BACKGROUND ART

Dipeptidyl peptidase IV (DPIV) is a serine protease which cleaves N-terminal dipeptides from a peptide chain containing, preferably, a proline residue in the penultimate position. Although the biological role of DPIV in mammalian systems has not been completely established, it is believed to play an important role in neuropeptide metabolism, T-cell activation, attachment of cancer cells to the endothelium and the entry of HIV into lymphoid cells.

Likewise, it was discovered that DPIV is responsible for inactivating glucagon-like peptide-1 (GLP-1) and glucose-dependent insulinotropic peptide also known as gastric-inhibitory peptide (GIP). Since GLP-1 is a major stimulator of pancreatic insulin secretion and has direct beneficial effects on glucose disposal, in WO 97/40832 and U.S. Pat. No. 6,303,661 inhibition of DPIV and DPIV-like enzyme activity was shown to represent an attractive approach e.g. for treating non-insulin-dependent diabetes mellitus (NIDDM). It is an aspect of the present invention to provide new DPIV inhibitors which are effective e.g. in treating conditions mediated by inhibition of DPIV and DPIV-like enzymes, pharmaceutical compositions e.g. useful in inhibiting DPIV and DPIV-like enzymes and a method of inhibiting said enzyme activity.

Another aspect of the invention relates to a method of treatment, in particular to a method for the treatment of diabetes mellitus, especially non-insulin dependent diabetes (NIDDM) or Type 2 diabetes and conditions associated with diabetes mellitus and to compositions for use in such method.

Dipeptidyl peptidase IV (DPIV) is a post-proline (to a lesser extent post-alanine, post-serine or post-glycine) cleaving serine protease found in various tissues of the body including kidney, liver, and intestine.

It is known that DPIV inhibitors may be useful for the treatment of impaired glucose tolerance and diabetes mellitus (International Patent Application, Publication Number WO 99/61431, Pederson R A et al, Diabetes. 1998 August; 47(8):1253–8 and Pauly R P et al, Metabolism 1999 March; 48(3):385–9). In particular WO 99/61431 discloses DPIV inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples for low molecular weight dipeptidyl peptidase IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, boronyl inhibitors and cyclopropyl-fused pyrrolidines. Inhibitors of dipeptidyl peptidase IV are described in U.S. Pat. Nos. 6,011,155; 6,107,317; 6,110,949; 6,124,305; 6,172,081; WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105 and WO 02/02560, the teachings of which are herein incorporated by reference in their entirety concerning the inhibitors, their production and their use.

SUMMARY OF THE INVENTION

The present invention provides a compound of the formula:

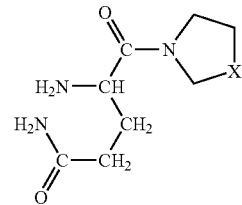

wherein X=CH$_2$ or S or a pharmaceutically acceptable salt thereof.

Such compounds and their corresponding pharmaceutically acceptable acid addition salt forms, are useful in treating conditions mediated by DPIV or DPIV-like enzymes, such as arthritis, obesity, immune and autoimmune disorders, allograft transplantation, cancer, neuronal disorders and dermal diseases.

In a more preferred embodiment, the compounds of the present invention improve glucose tolerance by lowering elevated blood glucose levels-in response to an oral glucose challenge and, therefore, are useful in treating non-insulin-dependent diabetes mellitus.

BRIEF DESCRIPTION OF THE DRAWINGS

Further understanding of the present invention may be had by reference to the figures wherein.

DETAILED DESCRIPTION OF THE INVENTION

Figure 1:
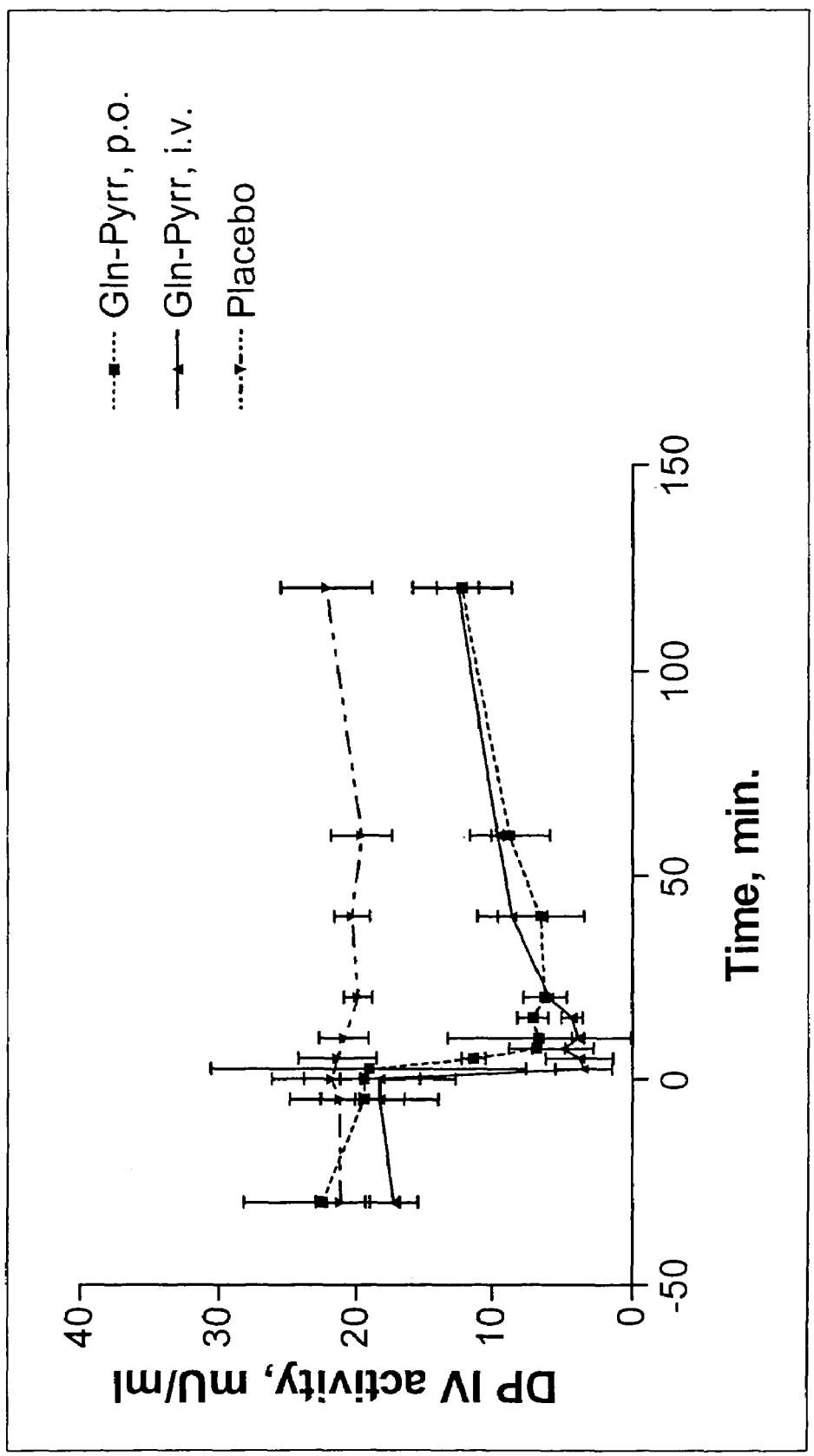
FIG. 1 shows the plasma DPIV activity in Wistar rat serum after oral and intra-vasal administration of 100 mg/kg b.w. glutaminyl pyrrolidine.

The present invention relates to the area of dipeptidyl peptidase IV (DPIV) inhibition and, more particularly, relates to glutaminyl pyrrolidine and glutaminyl thiazolidine, pharmaceutical compositions containing said compounds, and the use of said compounds in inhibiting DPIV and DPIV-like enzyme activity.

The present invention provides new DPIV inhibitors, which are effective e.g. in treating conditions mediated by DPIV inhibition, pharmaceutical compositions e.g. useful in inhibiting DPIV and DPIV-like enzyme activity and a method of inhibiting DPIV and DPIV-like enzyme activity.

The present invention provides a compound of the formula:

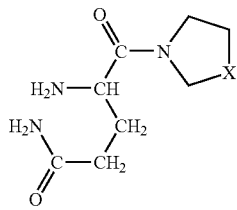

and especially a compound of the formula (I)

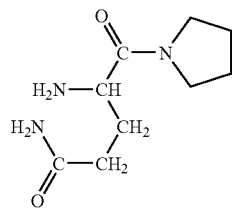

(I)

or a pharmaceutically acceptable salt thereof.

A further preferred compound of the present invention is the compound of formula II:

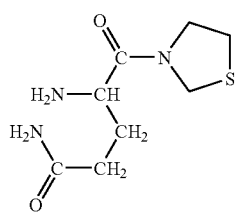

(II)

or a pharmaceutically acceptable salt thereof.

The compounds of the present invention can be converted into acid addition salts, especially pharmaceutically acceptable acid addition salts. The pharmaceutically acceptable salt generally takes a form in which an amino acids basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications. DE 198 28 113, DE 198 28 114, WO 99/67228 and WO 99/67279 which are fully incorporated herein by reference.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

As indicated above, the compounds of the present invention and especially the compounds of formulas I and II, and their corresponding pharmaceutically acceptable acid addition salt forms, are useful in inhibiting DPIV and DPIV-like enzyme activity. The ability of the compounds of the present invention, and their corresponding pharmaceutically acceptable acid addition salt forms to inhibit DPIV and DPIV-like enzyme activity may be demonstrated employing the DPIV activity assay for determination of the $K_i$-values in vitro and in human plasma, as described in examples 4 and 5. The $K_i$-values of the compounds of the present invention were determined for glutaminyl thiazolidine as $K_i=3.12*10^{-7}$ M±$5.11*10^{-10}$ M and for glutaminyl pyrrolidine as $K^i=1.30*10^{-6}$ M±$8.49*10^{-8}$ M against porcine kidney DPIV. The $K_i$-values of the compounds of the present invention were determined for glutaminyl thiazolidine as $K^i=4.03*10^{-7}$ M±$2.19*10^{-10}$ M after 5 min $5.13*10^{-7}$ M±$1.26*10^{-8}$ M after 22 hours pre-incubation, and for glutaminyl pyrrolidine as $K_i=1.30*10^{-6}$ M±$4,89*10^{-8}$ M after 5 min and $1.36*10^{-6}$ M±$3,21*10^{-8}$ M after 22 hours pre-incubation in human plasma.

The ability of the compounds of the present invention, and their corresponding pharmaceutically acceptable acid addition salt forms to inhibit DPIV in vivo may be demonstrated by oral or intravasal administration to Wistar rats, as described in example 9. The compounds of the present invention inhibit DPIV activity in vivo after both, oral and intravasal administration to Wistar rats.

DPIV is present in a wide variety of mammalian organs and tissues e.g. the intestinal brush-border (Gutschmidt S. et al., "In situ"—measurements of protein contents in the brush border region along rat jejunal villi and their correlations with four enzyme activities. Histochemistry 1981, 72 (3), 467–79), exocrine epithelia, hepatocytes, renal tubuli, endothelia, myofibroblasts (Feller A. C. et al., A monoclonal antibody detecting dipeptidylpeptidase IV in human tissue. Virchows Arch. A. Pathol. Anat. Histopathol. 1986; 409 (2):263–73), nerve cells, lateral membranes of certain surface epithelia, e.g. Fallopian tube, uterus and vesicular gland, in the luminal cytoplasm of e.g., vesicular gland epithelium, and in mucous cells of Brunner's gland (Hartel S. et al., Dipeptidyl peptidase (DPP) IV in rat organs. Comparison of immunohistochemistry and activity histochemistry. Histochemistry 1988; 89 (2): 151–61), reproductive organs, e.g. cauda epididymis and ampulla, seminal vesicles and their secretions (Agrawal & Vanha-Perttula, Dipeptidyl peptidases in bovine reproductive organs and secretions. Int. J. Androl. 1986, 9 (6): 435–52). In human serum, two molecular forms of dipeptidyl peptidase are present (Krepela E. et al., Demonstration of two molecular forms of dipeptidyl peptidase IV in normal human serum. Physiol. Bohemoslov. 1983, 32 (6): 486–96). The serum high molecular weight form of DPIV is expressed on the surface of activated T cells (Duke-Cohan J. S. et al., Serum high molecular weight dipeptidyl peptidase IV (CD26) is similar to a novel antigen DPPT-L released from activated T cells. J. Immunol. 1996, 156 (5): 1714–21).

The compounds of the present invention, and their corresponding pharmaceutically acceptable acid addition salt forms are able to inhibit DPIV in vivo. In one embodiment of the present invention, all molecular forms, homologues and epitopes of DPIV from all mammalian tissues and organs, also of those, which are undiscovered yet, are intended to be embraced by the scope of this invention.

Among the rare group of proline-specific proteases, DPIV was originally believed to be the only membrane-bound enzyme specific for proline as the penultimate residue at the amino-terminus of the polypeptide chain. However, other molecules, even structurally non-homologous with the DPIV but bearing corresponding enzyme activity, have been identified recently. DPIV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? Biochimica et Biophysica Acta 2001, 36506: 1–10).

Further DPIV-like enzymes are disclosed in WO 01/19866, WO 02/04610, WO 02/34900 and WO02/31134. WO 01/19866 discloses novel human dipeptidyl aminopeptidase (DPP8) with structural und functional similarities to DPIV and fibroblast activation protein (FAP). WO 02/04610 provides reagents, which regulate human dipeptidyl peptidase IV-like enzyme and reagents which bind to human dipeptidyl peptidase IV-like enzyme gene product. These reagents can play a role in preventing, ameliorating, or correcting dysfunctions or diseases including, but not limited to, tumors and peripheral and central nervous system disorders including pain and neurodegenerative disorders. The dipeptidyl peptidase IV-like enzyme of WO 02/04610 is well known in the art. In the Gene Bank data base, this enzyme is registered as KIAA1492 (registration in February 2001, submitted on Apr. 4, 2000, AB040925). WO 02/34900 discloses a dipeptidyl peptidase 9 (DPP9) with significant homology with the amino acid sequences of DPIV and DPP8. WO 02/31134 discloses three DPIV-like enzymes, DPRP1, DPRP2 and DPRP3. Sequence analysis revealed, that DPRP1 is identical to DPP8, as disclosed in WO 01/19866, that DPRP2 is identical to DPP9 and that DPRP3 is identical to KIAA1492 as disclosed in WO 02/04610.

In another preferred embodiment of the present invention, all molecular forms, homologues and epitopes of proteins comprising DPIV-like enzyme activity, from all mammalian tissues and organs, also of those, which are undiscovered yet, are intended to be embraced by the scope of this invention.

The ability of the compounds of the present invention, and their corresponding pharmaceutically acceptable acid addition salt forms to inhibit DPIV-like enzymes may be demonstrated employing an enzyme activity assay for determination of the $K_i$-values in vitro as described in example 6. The $K_i$-values of the compounds of the present invention against porcine dipeptidyl peptidase II were determined as $K_i=8.52*10^{-5}$ M±$6.33*10^{-6}$ M for glutaminyl pyrrolidine and $K_i=1.07*10^{-5}$ M±$3.81*10^{-7}$ M for glutaminyl thiazolidine. All compounds inhibit porcine dipeptidyl peptidase II.

In another embodiment of the present invention, the compounds of the present invention, and their corresponding pharmaceutically acceptable acid addition salt forms have only low, if no inhibitory activity against non-DPIV and non-DPIV-like proline specific enzymes. As described in example 7, with glutaminyl thiazolidine and glutaminyl pyrrolidine no inhibition of dipeptidyl peptidase I and prolyl oligopeptidase was found. Against prolidase, both compounds showed a marked lower efficacy compared to DPIV. The $IC_{50}$-values against prolidase were determined as $IC_{50}>3$ mM for glutaminyl thiazolidine and as $IC^{50}=3.4*10^{-4}$M±$5.63*10^{-5}$ for glutaminyl pyrrolidine.

In view of their ability to inhibit DPIV and DPIV-like enzyme activity, the compounds of the present invention, especially the compounds of formulas I and II, and their corresponding pharmaceutically acceptable acid addition salt forms, are useful in treating conditions mediated by said enzyme activities. Thus, the compounds disclosed herein are useful in the treatment of conditions such as non-insulin-dependent diabetes mellitus, arthritis, obesity, immune and autoimmune disorders, allograft transplantation, cancer, neuronal disorders like multiple sclerosis and dermal diseases.

In a more preferred embodiment of this invention, the compounds of the present invention and their corresponding pharmaceutically acceptable acid addition salt forms, improve glucose tolerance by lowering elevated blood glucose levels in response to an oral glucose challenge and, therefore, are useful in treating non-insulin-dependent diabetes mellitus. The ability of the compounds of the present invention, and their corresponding pharmaceutically acceptable acid addition salt forms, to improve glucose tolerance in response to an oral glucose challenge, may be measured in diabetic Zucker rats. The method is described in examples 10 and 11. Oral administration of 5 mg/kg b.w., 15 mg/kg and 50 mg/kg b.w. glutaminyl thiazolidine or glutaminyl pyrrolidine resulted in a dose dependent lowering of elevated blood glucose levels and thereby in an improvement of glucose tolerance in diabetic Zucker rats.

The compounds of the present invention are, according to example 5, stable in human plasma. Surprisingly, and as a further preferred embodiment of the present invention, the compounds of the present invention, and their corresponding pharmaceutically acceptable acid addition salt forms, may be degraded in vivo following administration to a mammal. The ability of the compounds of the present invention, and their corresponding pharmaceutically acceptable acid addition salt forms, to be degraded in vivo may be determined employing the Wistar rat model and subsequent LC/MS analysis. Glutaminyl thiazolidine was found to be degraded following oral administration. to Wistar rats, to the respective pyroglutaminyl thiazolidine.

The present invention therefore provides a method of treating a condition mediated by modulation of the DPIV or DPIV-like enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of the present invention, and their corresponding pharmaceutically acceptable acid addition salt forms, for the preparation of a medicament for the prevention or treatment of a condition mediated by modulation of the DPIV activity in a subject. The compound may be administered to a patient by any conventional route of administration, including, but not limited to, intravenous, oral, subcutaneous, intramuscular, intradermal and parenteral.

In an further embodiment, the present invention provides formulations for the compounds of the present invention, and their corresponding pharmaceutically acceptable acid addition salt forms, in pharmaceutical compositions.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, being sought by a researcher, veterinarian, medical doctor or other clinician, which includes alleviation of the symptoms of the disease or disorder being treated.

As used herein, the term "composition" is intended to encompass a product comprising the claimed compounds in the therapeutically effective amounts, as well as any product which results, directly or indirectly, from combinations of the claimed compounds.

To prepare the pharmaceutical compositions of this invention, one or more compounds of the present invention, especially compounds of the formulas I or II, and their corresponding pharmaceutically acceptable acid addition salt forms, as the active ingredient, are intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are employed. If desired, tablets may be sugar coated or enteric coated by standard techniques. For parenterals, the carrier will usually comprise sterile water, through other ingredients, for example, for purposes such as aiding solubility or for preservation, may be included.

Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per dosage unit, e.g., tablet, capsule, powder, injection, suppository, teaspoonful and the like, of from about 0.01 mg to about 1000 mg (preferably about 5 to about 500 mg) and may be given at a dosage of from about 0.1 to about 300 mg/kg bodyweight per day (preferably 1 to 50 mg/kg per day). The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from about 0.1 to about 1000 mg, preferably from about 5 to about 500 mg of the active ingredient of the present invention.

The tablets or pills of the novel composition can be advantageously coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be advantageously incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991, fully incorporated herein by reference. The protecting groups may be removed at a convenient subsequent stage using methods known from the art.

The method of treating conditions modulated by dipeptidyl peptidase IV and DPIV-like enzymes described in the present invention may also be carried out using a pharmaceutical composition comprising one or more of the compounds as defined herein and a pharmaceutically acceptable carrier. The pharmaceutical composition may contain between about 0.01 mg and 1000 mg, preferably about 5 to about 500 mg, of the compounds, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

More preferably, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms are suitable in flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, poly-epsilon caprolactone, polyhydroxy butyeric acid, poly-orthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of the addressed disorders is required.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

The compounds or compositions of the present invention may be taken before a meal, while taking a meal or after a meal.

When taken before a meal the compounds or composition of the present invention an be taken 1 hour, preferably 30 or even 15 or 5 minutes before eating.

When taken while eating, the compounds or compositions of the present invention can be mixed into the meal or taken in a separate dosage form as described above.

When taken after a meal, the compounds or compositions of the present invention can be taken 5, 15 or 30 minutes or even 1 hour after finishing a meal.

EXAMPLES

Example 1

Synthesis of Glutaminyl Pyrrolidine Free Base

Acylation:

N-Benzyl-oxycarbonylglutamine (2.02 g, 7.21 mmol) was dissolved in 35 ml THF and brought to −15° C. Into that mixture CAIBE (isobutylchloroformiate) (0.937 ml, 7.21 mmol) and 4-methylmorpholine (0.795 ml, 7.21 mmol) where added and the solution was stirred for 15 min The formation of the mixed anhydride was checked by TLC (eluent: $CHCl_3$/MeOH: 9/1). After warming to −10° C. pyrrolidine (0.596 ml, 7.21 mmol) was added. The mixture was brought to room temperature and stirred overnight.

Workup:

The sediment formed was filtered off and the solvent was evaporated. The resulting oil was taken up in ethylacetate (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 1.18 g, waxy solid

Cleavage:

1.18 g of the resulting solid Z-protected compound was dissolved in 40 ml absolute ethanol. Into the solution ca. 20 mg Pd on charcoal (10%, FLUKA) was added and the suspension was shaken under a hydrogen athmosphere for 3 h. The progress of the reaction was monitored by TLC (eluent: $CHCl_3$/MeOH: 9/1). After completion of the reaction the was removed to provide the free base.

Yield: 99%

The purity was checked by means of TLC: n-butanole/AcOH/water/ethylacetate: 1/1/1/1, $R_f$=0.4.

The identity of the reaction product was checked by NMR analysis.

Example 2

Synthesis of Glutaminyl Thiazolidine Hydrochloride

Acylation:

N-t-Butyl-oxycarbonylglutamine (2.0 g, 8.12 mmol) was dissolved in 5 ml THF and brought to −15° C. Into that mixture CAIBE (isobutylchloroformiate) (1,06 ml, 8.12 mmol) and 4-methylmorpholine (0.895 ml, 8.12 mmol) where added and the solution was stirred for 15 min The formation of the mixed anhydride was checked by TLC (eluent: $CHCl_3$/MeOH: 9/1). After warming to −10° C. another equivalent 4-methylmorpholine (0.895 ml, 8.12 mmol) and thiazolidinehydrochloride (1.02 g, 8.12 mmol) was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 1.64 g, solid

Cleavage:

640 mg of the resulting solid Boc-protected compound was dissolved in 3.1 ml ice cold HCl in dioxane (12.98 M, 20 equivalents) and left on ice. The progress of the reaction was monitored by TLC (eluent: $CHCl_3$/MeOH: 9/1). After completion of the reaction the solvent was removed and the resulting oil was taken up in methanole and evaporated again. After that the resulting oil was dried over phosphorous-V-oxide and triturated two times with diethylether. The purity was checked by HPLC.

Yield: 0.265 g

The purity was checked by HPLC.

The identity of the reaction product was checked by NMR analysis.

Example 3

Synthesis of Glutaminyl Pyrrollidine Hydrochloride

Acylation:

N-t-Butyl-oxycarbonylglutamine (3.0 g, 12.18 mmol) was dissolved in 7 ml THF and brought to −15° C. Into that mixture CAIBE (isobutylchloroformiate) (1,6 ml, 12.18 mmol) and 4-methylmorpholine (1.3 ml, 12.18 mmol) where added and the solution was stirred for 15 min The formation of the mixed anhydride was checked by TLC (eluent: $CHCl_3$/MeOH: 9/1). After warming to −10° C. 1 equivalent of pyrrolidine (1.0 ml, 12.18 mmol) was added. The mixture was brought to room temperature and stirred overnight.

Workup:

The sediment formed was filtered off and the solvent was evaporated. The resulting oil was taken up in chloroform (20 ml) and washed with a saturated solution of sodiumhydrogensulfate followed by a saturated solution of sodiumbicarbonate, water and brine. The organic layer was separated, dried and evaporated. The resulting product was checked for purity by TLC (eluent: $CHCl_3$/MeOH: 9/1)

Yield: 2.7 g solid

Cleavage:

2.7 g of the resulting solid was dissolved in 13.0 ml ice cold HCl in dioxane (12.98 M, 20 equivalents) and left on ice. The progress of the reaction was monitored by TLC (eluent: $CHCl_3$/MeOH: 9/1). After completion of the reaction the solvent was removed and the resulting oil was taken up in methanole and evaporated again. After that the resulting oil was dried over phosphorous-V-oxide and triturated two times with diethylether.

Yield: 980 mg

The purity was checked by HPLC.

The identity of the reaction product was checked by NMR analysis.

Example 4

$K_i$-determination

For $K_i$ determination of glutaminyl pyrrolidine and glutaminyl thiazolidine, dipeptidyl peptidase IV from porcine kidney with a specific activity against glycylprolyl-4-nitroaniline of 37.5 U/mg and an enzyme concentration of 1.41 mg/ml in the stock solution was used.

Assay Mixture:

100 µl glutaminyl pyrrolidine or glutaminyl thiazolidine in a concentration range of $1*10^{-5}$ M–$1*10^{-7}$ M (glutaminyl pyrrolidine) and $1*10^{-6}$ M–$1*10^{-8}$ M (glutaminyl thiazolidine) respectively were admixed with 50 µl glycylprolyl-4-nitroaniline in different concentrations (0.4 mM, 0.2 mM, 0.1 mM, 0,05 mM) and 100 µl HEPES (40 mM, pH7.6; ion strength=0.125). The assay mixture was pre-incubated at 30° C. for 30 min After pre-incubation, 20 µl DPIV (1:600 diluted) were added and measurement of yellow color development due to 4-nitroaniline release was performed at 30° C. and λ=405 nm for 10 min using a plate reader (HTS7000 plus, Applied Biosystems, Weiterstadt, Germany).

The $K_i$-values were calculated using Graphit 4.0.15 (Erithacus Software, Ltd, UK) based on a competitive inhibition of DPIV by glutaminyl pyrrolidine or glutaminyl thiazolidine. They were determined for glutaminyl thiazolidine as $K_i=3.12*10^{-7}$ M$\pm 5.11*10^{-10}$ M and for glutaminyl pyrrolidine as $K_i=1.30*10^{-6}$ M$\pm 8.49*10^{-8}$ M.

Example 5

$K_i$-determination in Human Plasma

Human plasma contains N-terminal Xaa-Pro releasing activity.

70 µl glutaminyl pyrrolidine or glutaminyl thiazolidine in an concentration range of $1*10^{-5}$ M–$1*10^{-7}$ M (glutaminyl pyrrolidine) and $1*10^{-6}$ M–$1*10^{-8}$ M (glutaminyl thiazolidine) respectively were admixed with 50 µl glycylprolyl-4-nitroaniline in different concentrations (0.4 mM, 0.2 mM, 0.1 mM, 0,05 mM) and 100 µl HEPES (40 mM, pH7.6). The assay mixture was pre-incubated at 30° C. for 5 min and 22 hours respectively. After pre-incubation, 50 µl human plasma were added and measurement of yellow color development due to 4-nitroaniline release was performed at 30° C. and λ=405 nm for 10 min using a plate reader (HTS7000 plus, Applied Biosystems, Weiterstadt, Germany).

The $K_i$-values were calculated using Graphit 4.0.15 (Erithacus Software, Ltd, UK) based on a competitive inhibition of DPIV by glutaminyl pyrrolidine or glutaminyl thiazolidine. They were determined for glutaminyl thiazolidine as $K_i=4.03*10^{-7}$ M$\pm 2.19*10^{-10}$ M after 5 min $5.13*10^{-7}$ M$\pm 1.26*10^{-8}$ M after 22 hours pre-incubation, and for glutaminyl pyrrolidine as $K_i=1.30*10^{-6}$ M$\pm 4,89*10^{-8}$ M after 5 min and $1.36*10^{-6}$ M$\pm 3,21*10^{-8}$ M after 22 hours pre-incubation.

Example 6

Inhibition of DPIV-like Enzymes—Dipeptidyl Peptidase II

DP II (3.4.14.2) releases N-terminal dipeptides from oligopeptides if the N-terminus is not protonated (McDonald, J. K., Ellis, S. & Reilly, T. J., 1966, *J. Biol. Chem.*, 241, 1494–1501). Pro and Ala in $P_1$-position are preferred residues. The enzyme activity is described as DPIV-like activity, but DP II has an acidic pH-optimum. The enzyme used was purified from porcine kidney.

Assay:

100 µl glutaminyl pyrrolidine or glutaminyl thiazolidine in an concentration range of $1*10^{-4}$ M–$5*10^{-8}$ M were admixed with 100 µl µl buffer solution (40 mM HEPES, pH7.6, 0.015% Brij, 1 mM DTT), 50 µl lysylalanylaminomethylcoumarine solution (5 mM) and 20 µl porcine DP II (250fold diluted in buffer solution). Fluorescence measurement was performed at 30° C. and $\lambda_{exiatation}$=380 nm, $\lambda_{emission}$=465 nm for 25 min using a plate reader (HTS7000plus, Applied Biosystems, Weiterstadt, Germany).

The $K_i$-values were calculated using Graphit 4.0.15 (Erithacus Software, Ltd., UK) and were determined as $K^i=8.52*10^{-5}$ M $6.33*10^{-6}$ M for glutaminyl pyrrolidine and $K_i=1.07*10^{-5}$ M$\pm 3.81*10^{-7}$ M for glutaminyl thiazolidine.

Example 7

Cross Reacting Enzymes

Glutaminyl pyrrolidine or glutaminyl thiazolidine were tested for their cross reacting potency against dipeptidyl peptidase I, prolyl oligopeptidase and prolidase.

Dipeptidyl Peptidase I (DP I, Cathepsin C):

DP I or cathepsin C is a lysosomal cysteine protease which cleaves off dipeptides from the N-terminus of their substrates (Gutman, H. R. & Fruton, J. S., 1948, *J. Biol: Chem.*, 174, 851–858) . It is classified as a cysteine protease.

The enzyme used was purchased from Qiagen (Qiagen GmbH, Hilden, Germany). In order to get a fully active enzyme, the enzyme was diluted 1000fold in MES buffer pH5,6 (40 mM MES, 4 mM DTT, 4 mM KCl, 2 mM EDTA, 0.015% Brij) and pre-incubated for 30 min at 30° C.

Assay:

50 µl glutaminyl pyrrolidine or glutaminyl thiazolidine in a concentration range of $1*10^{-5}$ M–$1*10^{-7}$ M were admixed with 110 µl buffer-enzyme-mixture. The assay mixture was pre-incubated at 30 ° C. for 15 min After pre-incubation, 100 µl histidylseryl-β-nitroaniline ($2*10^{-5}$M) were added and measurement of yellow color development due to β-nitroaniline release was performed at 30° C. and $\lambda_{excitation}$=380 nm, $\lambda_{emission}$=465 nm for 10 min, using a plate reader (HTS7000 plus, Applied Biosystems, Weiterstadt, Germany).

The $IC_{50}$-values were calculated using Graphit 4.0.15 (Erithacus Software, Ltd., UK). No inhibition of the DP I enzyme activity by glutaminyl pyrrolidine or glutaminyl thiazolidine was found.

Prolyl Oligopeptidase (POP)

Prolyl oligopeptidase (EC 3.4.21.26) is a serine type endoprotease which cleaves off peptides at the N-terminal part of the Xaa-Pro bond (Walter, R., Shlank, H., Glass, J. D., Schwartz, I. L. & Kerenyi, T. D., 1971, *Science*, 173, 827–829). Substrates are peptides with a molecular weight up to 3000 Da.

The enzyme used was a recombinant human prolyl oligopeptidase. Recombinant expression was performed in *E. coli* under standard conditions as described elsewhere in the state of the art.

Assay:

100 µl glutaminyl pyrrolidine or glutaminyl thiazolidine in an concentration range of $1*10^{-4}$ M–$5*10^{-8}$ M were admixed with 100 µl µl buffer solution (40 mM HEPES, pH7.6, 0.015% Brij, 1 mM DTT) and 20 µl POP solution. The assay mixture was pre-incubated at 30° C. for 15 min After pre-incubation, 50 µl glycylprolylprolyl-4-nitroaniline solution (0.29 mM) were added and measurement of yellow color development due to 4-nitroaniline release was performed at 30° C. and λ=405 nm for 10 min using a plate reader (sunrise, Tecan, Crailsheim, Germany).

The $IC_{50}$-values were calculated using Graphit 4.0.15 (Erithacus Software, Ltd., UK). No inhibition of POP activity by glutaminyl pyrrolidine or glutaminyl thiazolidine was found.

Prolidase (X-Pro Dipeptidase)

Prolidase (EC 3.4.13.9) was first described by Bergmann & Fruton (Bergmann, M. & Fruton, J S, 1937, *J. Biol. Chem.* 189–202). Prolidase releases the N-terminal amino acid from Xaa-Pro dipeptides and has a pH optimum between 6 and 9.

Prolidase from porcine kidney (ICN Biomedicals, Eschwege, Germany). was solved (1 mg/ml) in assay buffer (20 mM $NH_4(CH_3COO)_2$, 3 mM $MnCl_2$, pH 7.6). In order to get a fully active enzyme the solution was incubated for 60 min at room temperature.

Assay:

450 µl glutaminyl pyrrolidine or glutaminyl thiazolidine in an concentration range of $5*10^{-3}$ M–$5*10^{-7}$ M were admixed with 500 µl buffer solution (20 mM $NH_4$ $(CH_3COO)_2$, pH 7.6) and 250 µl Ile-Pro-OH (0.5 mM in the assay mixture). The assay mixture was pre-incubated at 30° C. for 5 min After pre-incubation, 75 µl Prolidase (1:10 diluted in assay buffer) were added and measurement was performed at 30° C. and λ=220 nm for 20 min using a UV/Vis photometer, UV1 (Thermo Spectronic, Cambridge, UK).

The $IC_{50}$-values were calculated using Graphit 4.0.15 (Erithacus Software, Ltd., UK). They were determined as IC 50>3 mM for glutaminyl thiazolidine and as $IC^{50}=3.4*10^{-4}M\pm5.63*10^{-5}$ for glutaminyl pyrrolidine.

Example 8

Plasma Stability

In order to investigate the stability of glutaminyl pyrrolidine or glutaminyl thiazolidine in human plasma, the activity of DPIV in plasma was determined at a defined time. The average DPIV activity in human plasma was determined as 43.69 U/ml. In the working solution, the plasma was diluted in 0.9% NaCl to fix the DPIV activity level at 25 U/ml.

Plasma and glutaminyl pyrrolidine or glutaminyl thiazolidine in different concentrations ($5*10^{-5}$, $2.5*10^{-5}$, $1.25*10^{-5}$M in plasma) were incubated at 37° C. At defined time points samples were taken using a pipette roboter (Gilson 215, Liquid handler, Gilson) and transferred in a microtiter plate containing $5*10^{-5}$M glycylprolylaminomethylcoumarine in 0.9% NaCl+015% Brij per well. After 6 min the reaction was stopped by addition of isoleucylthiazolidine ($5*10^{-5}$M in 0.9% NaCl solution).

Fluorescence measurement was performed against 0.9% NaCl in plasma (reference standard) using a plate reader (HTS7000plus, Applied Biosystems, Weiterstadt, Germany). The half-life of the inhibitory potency of glutaminyl pyrrolidine or glutaminyl thiazolidine was calculated by plotting the enzyme activity versus reaction time.

For both compounds, no half-time could be determined. The substance is considered to be stable in human plasma over 22 hours.

Example 9

Determination of DPIV Inhibiting Activity of Glutaminyl Pyrrolidine and Glutaminyl Thiazolidine After Intravasal and Oral Administration to Wistar Rats Animals Male Wistar rats (Shoe: Wist(Sho)) with a body weight ranging between 250 and 350 g were purchased from Tierzucht Schönwalde (Schönwalde, Germany).

Housing Conditions

Animals were single-caged under conventional conditions with controlled temperature (22±2° C.) on a 12/12 hours light/dark cycle (light on at 06:00 AM). Standard pelleted chow (ssniff® Soest, Germany) and tap water acidified with HCl were allowed ad libitum.

Catheter Insertion into Carotid Artery

After≧one week of adaptation at the housing conditions, catheters were implanted into the carotid artery of Wistar rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of catheter dysfunction, a second catheter was inserted into the contra-lateral carotid artery of the respective rat. After one week of recovery from surgery, this animal was reintegrated into the study. In case of dysfunction of the second catheter, the animal was withdrawn from the study. A new animal was recruited and the experiments were continued in the planned sequence, beginning at least 7 days after catheter implantation.

Experimental Design

To rats with intact catheter function were administered placebo (1 ml saline, 0.154 mol/l ) or 100 mg/kg b.w. glutaminyl pyrrolidine or 100 mg/kg b.w. glutaminyl thiazolidine via the oral and the intra-vasal (intra-arterial) route.

After overnight fasting, 100 µl samples of heparinised arterial blood were collected at −30, −5, and 0 min The test substance was dissolved freshly in 1.0 ml saline (0.154 mol/l) and was administered at 0 min either orally via a feeding tube (75 mm; Fine Science Tools, Heidelberg, Germany) or via the intra-vasal route. In the case of oral administration, an additional volume of 1 ml saline was injected into the arterial catheter.

In the case of intra-arterial administration, the catheter was immediately flushed with 30 µl saline and an additional 1 ml of saline was given orally via the feeding tube. After application of placebo or the test substances, arterial blood samples were taken at 2.5, 5, 7.5, 10, 15, 20, 40, 60 and 120 min from the carotid catheter of the conscious unrestrained rats. All blood samples were collected into ice cooled Eppendorf tubes (Eppendorf-Netheler-Hinz, Hamburg, Germany) filled with 10 µl 1M sodium citrate buffer (pH 3.0) for plasma DPIV activity measurement. Eppendorf tubes were centrifuged immediately (12000 rpm for 2 min, Hettich Zentrifuge EBA 12, Tuttlingen; Germany): The plasma fractions were stored on ice until analysis or were frozen at −20° C. until analysis. All plasma samples were labelled with the following data:

Code number
Animal Number
Date of sampling
Time of sampling

Analytical Methods

The assay mixture for determination of plasma DPIV activity consisted of 80 µl reagent and 20 µl plasma sample. Kinetic measurement of the formation of the yellow product 4-nitroaniline from the substrate glycylprolyl-4-nitroaniline was performed at 390 nm for 1 min at 30° C. after 2 min pre-incubation at the same temperature. The DPIV activity was expressed in mU/ml.

Statistical Methods

Statistical evaluations and graphics were performed with PRISM® 3.02 (GraphPad Software, Inc.). All parameters were analysed in a descriptive manner including mean and SD.

RESULTS

Figure 2:
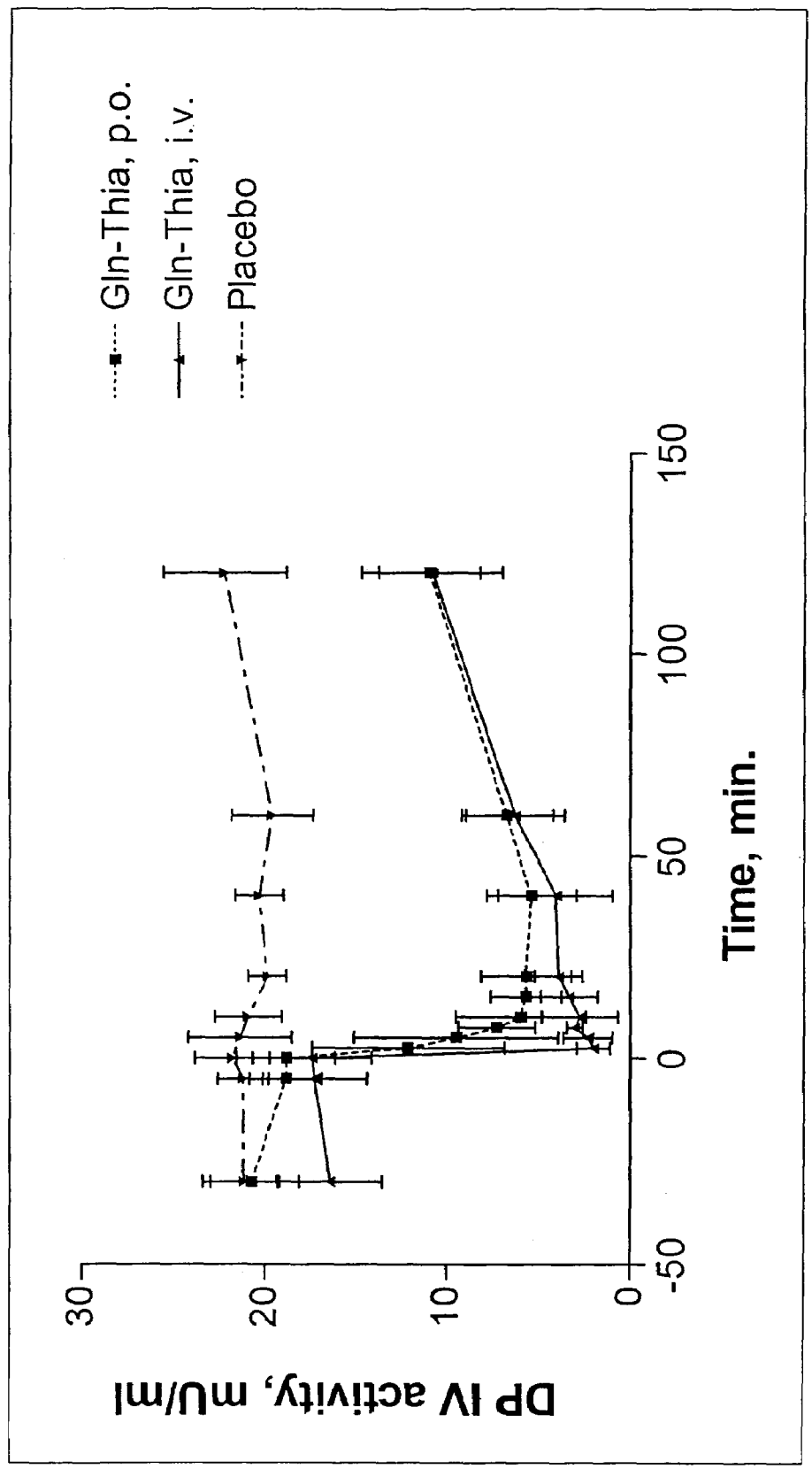
FIG. 2 shows the plasma DPIV activity in Wistar rat serum after oral and intra-vasal administration of 100 mg/kg b.w. glutaminyl thiazolidine.

The compounds glutaminyl pyrrolidine and glutaminyl thiazolidine in a dose of 100 mg/kg b.w. vs. placebo inhibited plasma DPIV activity after oral and intra-vasal administration (see FIGS. 1 and 2)

Example 10

Dose Escalation Study in Fatty Zucker Rats After Oral Administration of Glutaminyl Pyrrolidine Animals N=30 male Zucker rats (fa/fa), mean age 11 weeks (5–12 weeks), mean body weight 350 g (150–400 g), were purchased from Charles River (Sulzfeld, Germany). After delivery they were kept for >12 weeks until nearly all fatty Zucker rats had the characteristics of manifest diabetes mellitus. A group of N=8 animals were recruited for testing three escalating doses of glutaminyl pyrrolidine vs. placebo (saline).

Housing Conditions

Animals were single-caged under standardized conditions with controlled temperature (22±2° C.) on a 12/12 hours light/dark cycle (light on at 06:00 AM). Sterile standard pelleted chow (ssniff® Soest, Germany) and tap water acidified with HCl were allowed ad libitum.

Catheterization of Carotid Artery

Fatty Zucker rats of 24–31 weeks (mean: 25 weeks) age, adapted to the housing conditions, were well prepared for the study.

Catheters were implanted into the carotid artery of fatty Zucker rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week.

Experimental Design

Placebo (1 ml saline, 0.154 mol/l) or escalating doses of glutaminyl pyrrolidine (5, 15 and 50 mg/kg b.w.) were administered to groups of N=8 fatty Zucker rats. 375 mg of glutaminyl pyrrolidine were dissolved in 1000 µl DMSO (E. Merck, Darmstadt; Germany [Dimethyl sulfoxide p.a.]).10 ml saline were added and 1 ml aliquots, each containing 34.09 mg of glutaminyl pyrrolidine, were stored at −20° C. For preparation of the test substance, dose dependent aliquots were diluted in saline.

After overnight fasting, placebo or test substance were administered to the fatty Zucker rats via feeding tube orally (15 G, 75 mm; Fine Science Tools, Heidelberg, Germany) at −10 min An oral glucose tolerance test (OGTT) with 2 g/kg b.w. glucose (40% solution, B. Braun Melsungen, Melsungen, Germany) was administered at ±0 min via a second feeding tube. Venous blood samples from the tail veins were collected at −30 min, −15 min, ±0 min and at 5, 10, 15, 20, 30, 40, 60, 90 and 120 min into 20 µl glass capillaries, which were placed in standard tubes filled with 1 ml solution for blood glucose measurement.

All blood samples were labelled with the following data:

Code number
Animal Number
Date of sampling
Time of sampling

Analytical Methods

Glucose levels were measured using the glucose oxidase procedure (Super G Glucose analyzer; Dr. Müller Gerätebau, Freital, Germany).

Statistical Methods

Statistical evaluations and graphics were performed with PRISM® 3.02 (GraphPad Software, Inc.). All parameters were analysed in a descriptive manner including mean and SD.

Effect of Medication on Glucose Tolerance

Figure 3:
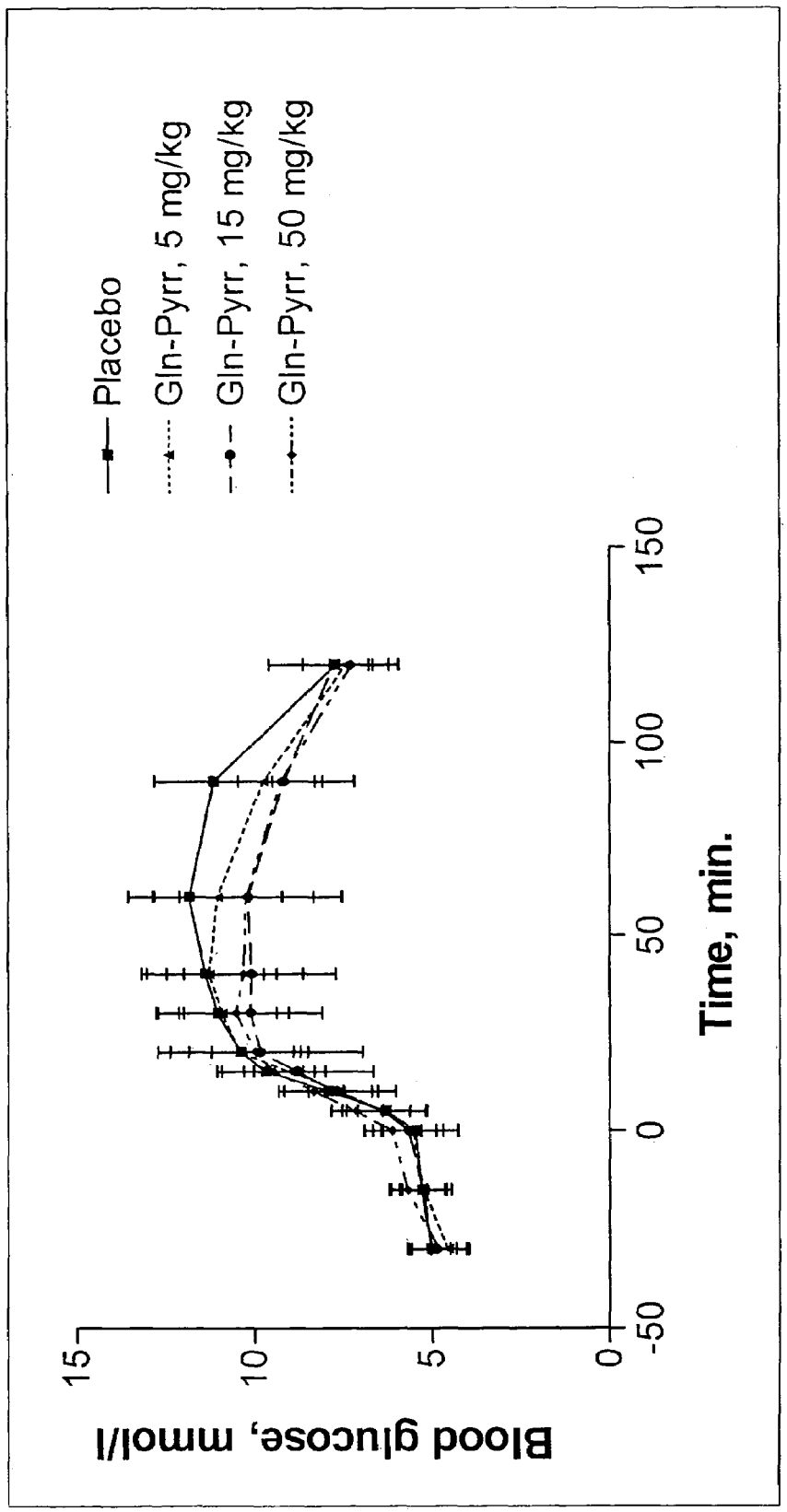
FIG. 3 shows the dose dependent lowering of blood glucose levels in diabetic Zucker rats following oral administration of 5 mg/kg, 15 mg/kg, 50 mg/kg b.w. glutaminyl pyrrolidine and placebo, respectively.

The placebo treated diabetic Zucker rats showed a strongly elevated blood glucose excursion indicating glucose intolerance of manifest diabetes mellitus. Administration of 5 mg/kg b.w. glutaminyl pyrrolidine resulted in a limited improvement of glucose tolerance in diabetic Zucker rats. Significant lowering of elevated blood glucose levels and improvement of glucose tolerance was achieved after administration of 15 mg/kg and 50 mg/kg b.w. glutaminyl pyrrolidine (see FIG. 3).

Example 11

Dose Escalation Study in Fatty Zucker Rats After Oral Administration of Glutaminyl Thiazolidine Animals N=30 male Zucker rats (fa/fa), mean age 11 weeks (5–12 weeks), mean body weight 350 g (150–400 g), were purchased from Charles River (Sulzfeld, Germany). After delivery they were kept for >12 weeks until nearly all fatty Zucker rats had the characteristics of manifest diabetes mellitus. A group of N=8 animals were recruited for testing three escalating doses of glutaminyl thiazolidine vs. placebo (saline).

Housing Conditions

Animals were single-caged under standardized conditions with controlled temperature (22±2° C.) on a 12/12 hours light/dark cycle (light on at 06:00 AM). Sterile standard pelleted chow (ssniff® Soest, Germany) and tap water acidified with HCl were allowed ad libitum.

Catheterization of Carotid Artery

Fatty Zucker rats of 24–31 weeks (mean: 25 weeks) age, adapted to the housing conditions, were well prepared for the study.

Catheters were implanted into the carotid artery of fatty Zucker rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week.

Experimental Design

Placebo (1 ml saline, 0.154 mol/l) or escalating doses of glutaminyl thiazolidine (5, 15 and 50 mg/kg b.w.) were administered to groups of N=8 fatty Zucker rats. The respective amounts of glutaminyl thiazolidine were dissolved in 1000 µl saline. After overnight fasting, placebo or test substance was administered to the fatty Zucker rats via feeding tube orally (15 G, 75 mm; Fine Science Tools, Heidelberg, Germany) at –10 min An oral glucose tolerance test (OGTT) with 2 g/kg b.w. glucose (40% solution, B. Braun Melsungen, Melsungen, Germany) was administered at ±0 min via a second feeding tube. Venous blood samples from the tail veins were collected at –30 min, –15 min, ±0 min and at 5, 10, 15, 20, 30, 40, 60, 90 and 120 min into 20 µl glass capillaries, which were placed in standard tubes filled with 1 ml solution for blood glucose measurement.

All blood samples were labelled with the following data:
Code number
Animal Number
Date of sampling
Time of sampling Analytical Methods Glucose levels were measured using the glucose oxidase procedure (Super G Glucose analyzer; Dr. Müller Gerätebau, Freital, Germany).

Statistical Methods

Statistical evaluations and graphics were performed with PRISM® 3.02 (GraphPad Software, Inc.). All parameters were analysed in a descriptive manner including mean and SD.

Effect of Medication on Glucose Tolerance

Figure 4:
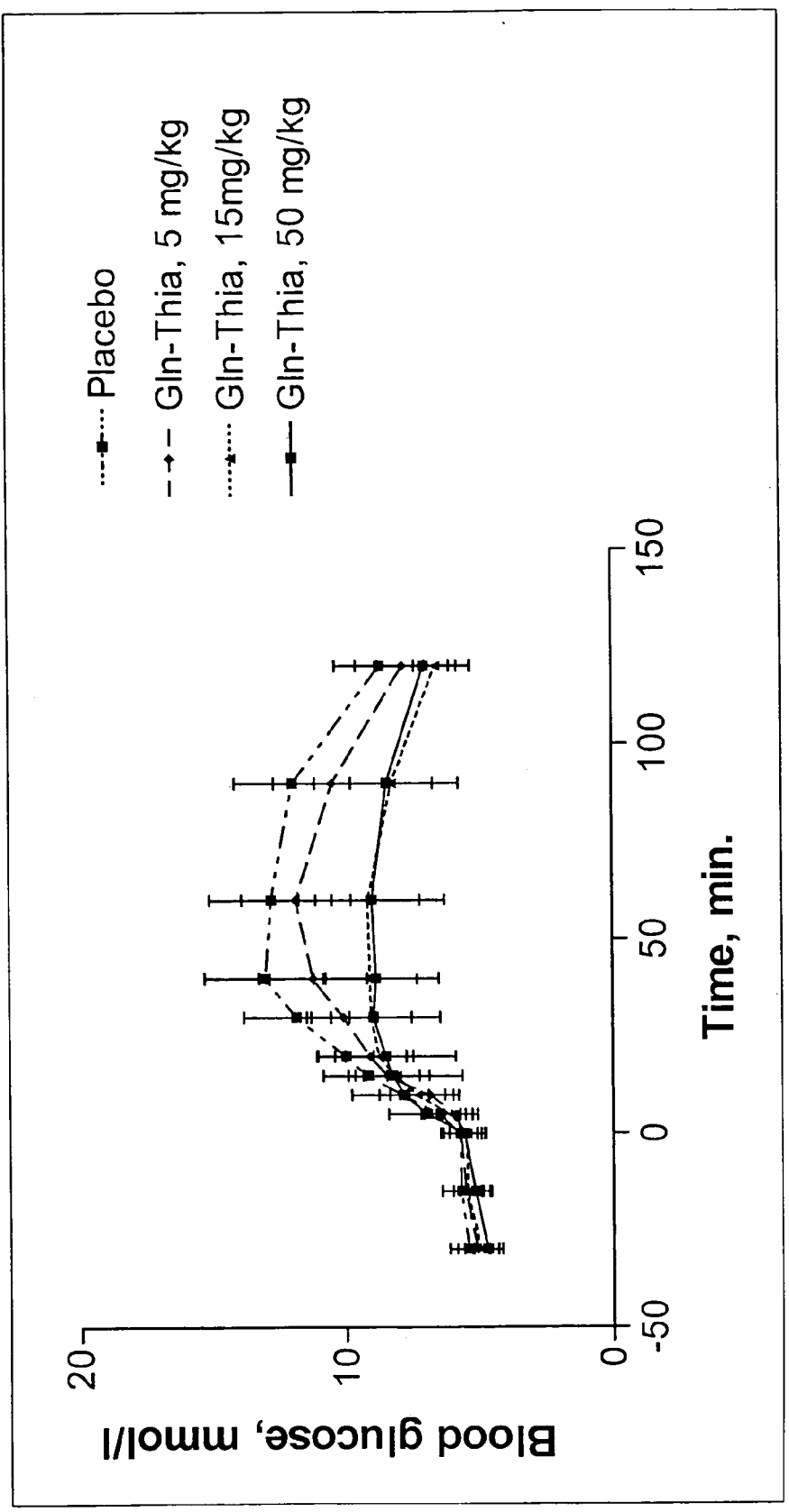
FIG. 4 shows the dose dependent lowering of blood glucose levels in diabetic Zucker rats following oral administration of 5 mg/kg, 15 mg/kg, 50 mg/kg b.w. glutaminyl thiazolidine and placebo, respectively.

The placebo treated diabetic Zucker rats showed a strongly elevated blood glucose excursion indicating glucose intolerance of manifest diabetes mellitus. Administration of 5 mg/kg b.w., 15 mg/kg and 50 mg/kg b.w glutaminyl thiazolidine resulted in a dose dependent lowering of elevated blood glucose levels and improvement of glucose tolerance in diabetic Zucker rats (see FIG. 4).

Example 12

In vivo Inactivation of Glutaminyl Thiazolidine After Oral Administration to Wistar Rats Animals/Experimental Design Glutaminyl thiazolidine was administered to Wistar rats orally as described in example 9.

Analytical Methods

After application of placebo or glutaminyl thiazolidine, arterial blood samples were taken at 2.5, 5, 7.5, 10, 15, 20, 40, 60 and 120 min from the carotid catheter of the conscious unrestrained rats to determine the formation of degradation products of glutaminyl thiazolidine.

For analysis, simple solid phase extraction procedure on C18 cartridges was used to isolate the compounds of interest from the plasma. The extracts were analysed using reversed-phase liquid chromatography on Lichrospher 60 RP Select B column hyphenated with tandem mass spectrometry operating in the APCl positive mode. An internal standard method was used for quantification.

Results

Figure 5:
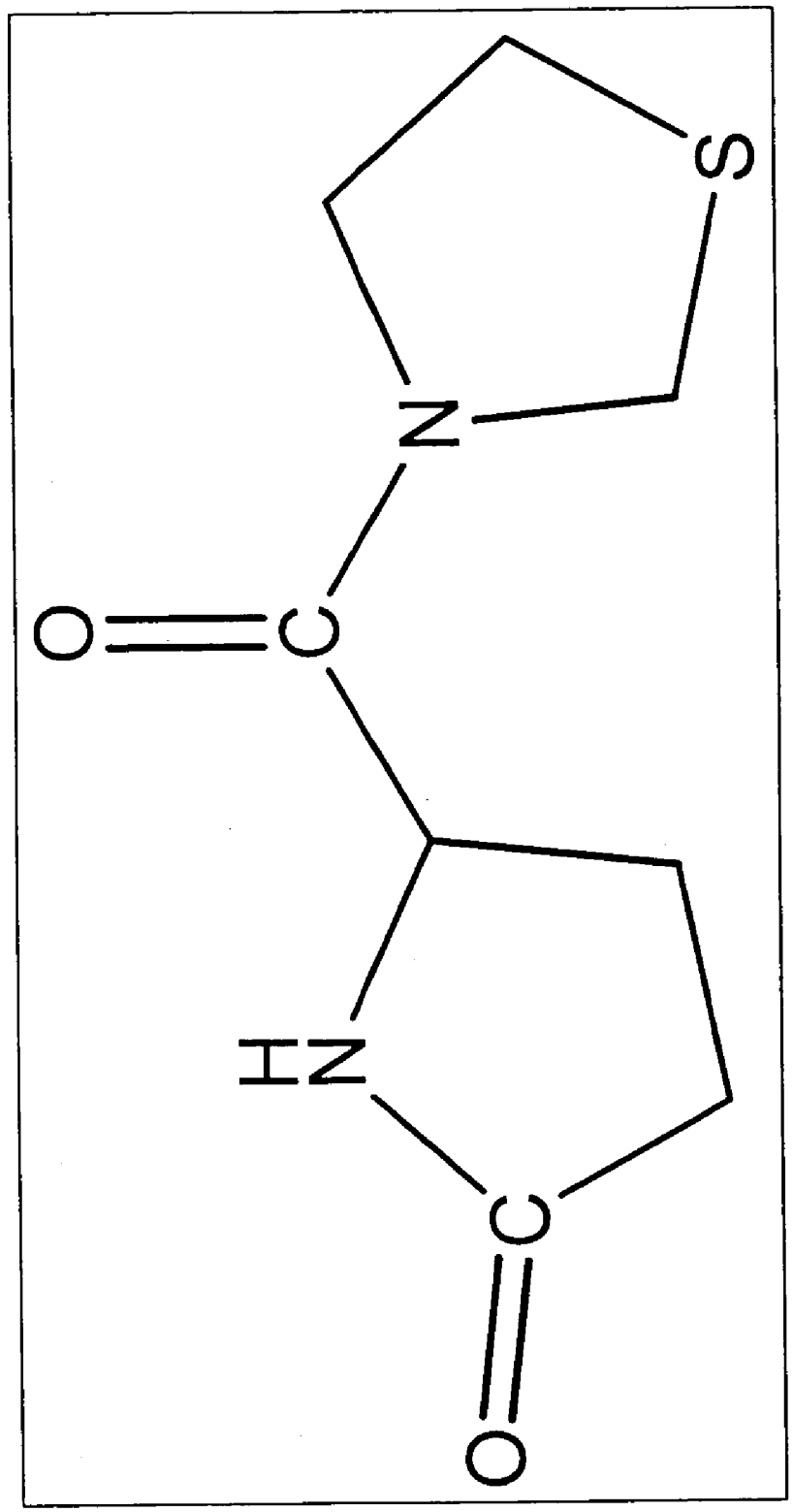
FIG. 5 shows the chemical structure of pyroglutaminyl thiazolidine, the degradation product, found after oral administration of glutaminyl thiazolidine to Wistar rats.
Figure 6:
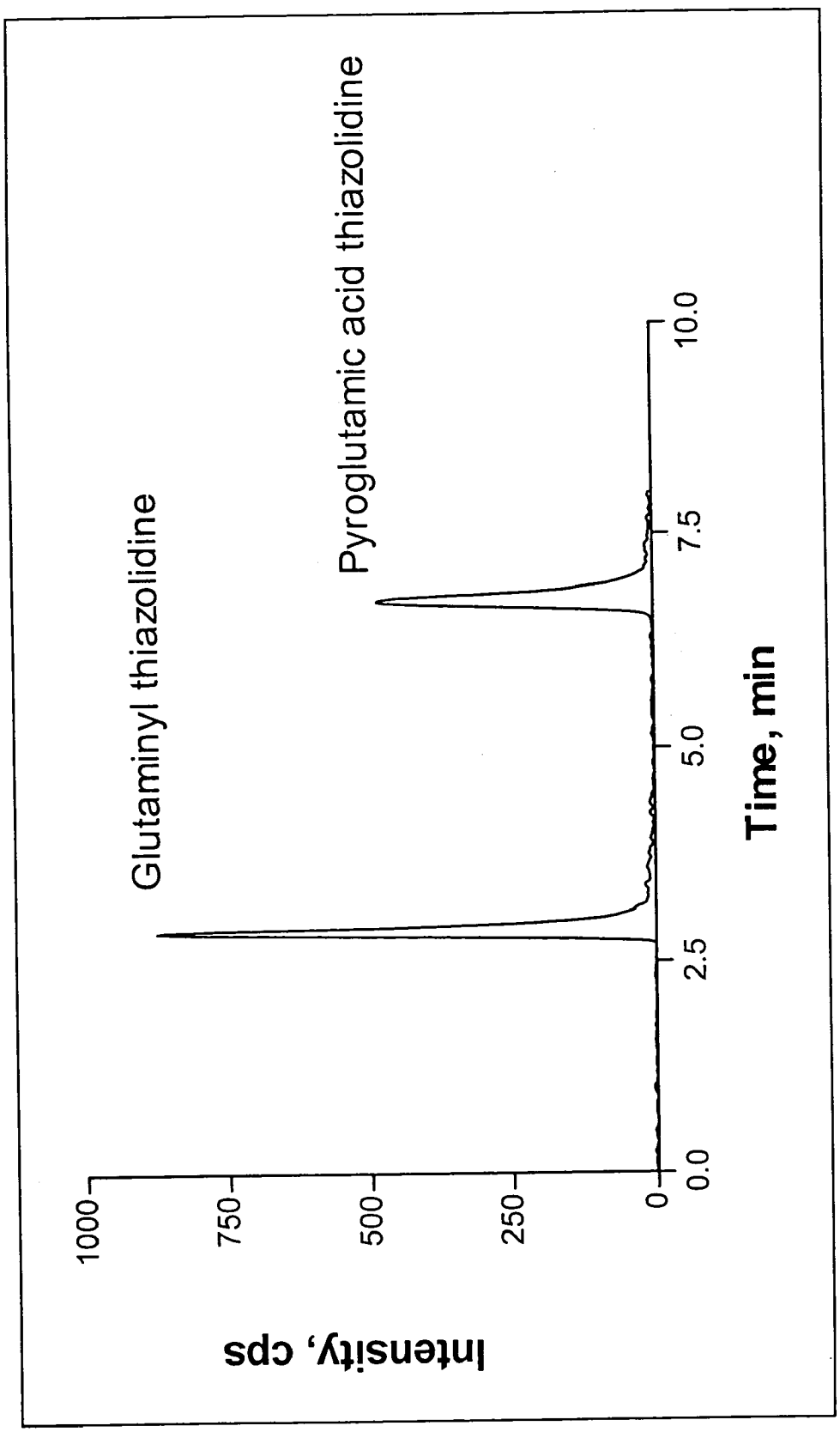
FIG. 6 shows the chromatogram of a rat plasma extract obtained after oral administration of glutaminyl thiazolidine to fatty Zucker rats. The peak at 2.95 min represents glutaminyl thiazolidine and the peak at 6.57 min represents pyroglutaminyl thiazolidine.

After oral administration of glutaminyl thiazolidine to Wistar rats, a degradation of the compound was found. Using LC/MS, the degradation product could be defined as pyroglutaminyl thiazolidine. (See FIGS. 5 and 6).

What is claimed is:

1. Acid addition salts of a compound of formula:

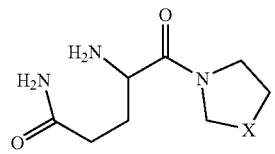

wherein X=$CH_2$ or S and wherein the acid addition salt is the hydrochloric salt.

2. A compound glutaminyl thiazolidine hydrocbioride.

3. The compound glutaminyl pyrrolidine hydrochloride.

4. A pharmaceutical composition comprising a pharmaceutically acceptable carrier and/or diluent and the compound of claim 1.

5. A pharmaceutical composition comprising a pharmaceutically acceptable carrier and/or diluent and the compound of claim 2.

6. A pharmaceutical composition comprising a pharmaceutically acceptable carrier and/or diluent and the compound of claim 3.

7. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising administering to a mammal in need of such treatment a therapeuticaily effective amount of the compound according to claim 1.

8. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising admninisteting to a mammal in need of such treatment a therapeutically effective amount of the compound accordiug to claim 2.

9. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising administering to a mammal in need of such treatment a therapeutically effective amount of the compound according to claim 3.

10. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising administering to a mammal in need of such treatment a therapeutically effective amount of the composition according to claim 4.

11. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising administering to a mammal in need of such treatment a therapeutically effective amount of the composition according to claim 5.

12. A method for inhibiting dipeptidyl peptidase IV or dipeptidyl peptidase IV-like enzyme activity for the treatment of diseases or conditions related to dipeptidyl peptidase IV or dipeptidyl peptidase IV-like enzymes selected from the group consisting of non-insulin-dependent diabetes mellitus, arthritis, obesity, immune and autoimmune disorders, allograft transplantation, cancer, neuronal disorders and dermal diseases comprising administering to a mammal in need of such treatment a therapeutically effective amount of the composition according to claim 6.

13. A method for inhibiting dipeptidyl peptidase IV or dipeptidyl peptidase IV-like enzyme activity for lowering elevated blood glucose levels in mammals resulting from food intake comprising administering to a mammal in need of such treatment a therapeutically effective amount of a compound according to claim 1.

14. A method for inhibiting dipeptidyl peptidase IV or dipeptidyl peptidase IV-like enzyme activity for lowering elevated blood glucose levels in mammals resulting from food intake comprising administering to a mammal in need of such treatment a therapeutically effective amount of the compound according to claim 2.

15. The method according to claim 8 for the treatment of a disease or condition selected from non-insulin-dependent diabetes mellitus, artbttis and obesity.

16. A method for inhibiting dipeptidyl peptidase IV or dipeptidyl peptidase IV-like enzyme activity for lowering elevated blood glucose levels in mammals resulting from food intake comprising administering to a mammal in need of such treatment a therapeutically effective amount of the compound according to claim 3.

17. The method according to claim 7 for the treatment of a disease or condition selected from non-insulin-dependent diabetes mellitus, arthritis and obesity.

18. The method according to claim 9 for the treatment of a disease or condition selected from non-insulin-dependent diabetes mellitus, arthritis and obesity.

\* \* \* \* \*